United States Patent [19]

Beestman et al.

[11] 4,159,901

[45] Jul. 3, 1979

[54] CORROSION INHIBITED AGRICULTURAL COMPOSITIONS

[75] Inventors: George B. Beestman, St. Louis; Erhard J. Prill, Kirkwood, both of Mo.

[73] Assignee: Monsanto Company, St. Louis, Mo.

[21] Appl. No.: 862,691

[22] Filed: Dec. 27, 1977

Related U.S. Application Data

[63] Continuation-in-part of Ser. No. 797,083, May 16, 1977, abandoned.

[51] Int. Cl.² ............................................. A01N 9/36
[52] U.S. Cl. ............................................. 71/86; 71/87;
  252/395; 422/12; 422/14; 422/15
[58] Field of Search ................. 71/86, 87; 252/395;
  422/12, 14, 15

[56] References Cited

U.S. PATENT DOCUMENTS

| | | | |
|---|---|---|---|
| 2,963,439 | 12/1960 | Eberhard | 252/395 X |
| 2,989,485 | 6/1961 | Eilers | 252/395 X |
| 3,455,675 | 7/1969 | Irani | 71/86 |
| 3,556,762 | 1/1971 | Hamm | 71/86 |
| 3,799,758 | 3/1974 | Franz | 71/86 |
| 3,853,530 | 12/1974 | Franz | 71/86 X |
| 3,868,407 | 2/1975 | Franz | 71/86 X |
| 3,971,648 | 7/1976 | Franz et al. | 71/86 |
| 3,977,860 | 8/1976 | Franz | 71/86 |
| 3,988,142 | 10/1976 | Franz | 71/86 |

Primary Examiner—Joseph P. Brust
Attorney, Agent, or Firm—William T. Black; Donald W. Peterson

[57] ABSTRACT

Corrosion of metal surfaces contacted by aqueous agricultural compositions containing as an active ingredient an aminomethylenephosphonic acid, such as N-phosphonomethylglycine or an agriculturally acceptable salt or ester thereof is inhibited by the inclusion in the compositions of an inhibiting amount of a thiol compound or salt thereof.

24 Claims, No Drawings

CORROSION INHIBITED AGRICULTURAL COMPOSITIONS

This application is a continuation-in-part of application Ser. No. 797,083, filed May 16, 1977 now abandoned.

This invention relates to the inhibition of metallic corrosion by aqueous agricultural compositions containing as an active agricultural ingredient an aminomethylenephosphonic acid, or an agriculturally acceptable salt or ester derivative thereof. More particularly, this invention relates to the inhibition of corrosion of iron or zinc surfaces contacted by aqueous agricultural compositions wherein the active agricultural ingredient, an aminomethylenephosphonic acid, or salt or ester derivatives thereof in the presence of water and in the absence of an inhibitor is corrosive of such surfaces and evolves hydrogen gas. According to this invention, corrosion of iron or zinc surfaces is inhibited by the inclusion in such agricultural composition of a corrosion inhibiting amount of a thiol compound or salt thereof as hereinafter described.

The aminomethylenephosphonic acids employed in the compositions of this invention are encompassed by the following formula

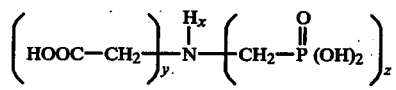

wherein y and z are each individually 1 or 2, and x is 0 or 1, the sum of x, y and z being 3. Also useful in the compositions of this invention are the agriculturally acceptable salts and esters of these acids.

The term "agricultural composition" as herein employed includes within its scope herbicidal and plant growth regulant compositions. While such compositions are frequently formulated as dry powder compositions and used in this form to dust plant foliage, more commonly they are formulated into solutions, emulsions, suspensions or dispersions for wet application to plant foliage. These liquid formulations usually contain water and more water is added thereto at the time of application in order to dilute the concentration of the active ingredient in the formulation to levels enabling the application of predetermined, controlled amounts to plant foliage. Normally, the dry powder formulations are generally non-corrosive of metal surfaces whereas depending on the specific active ingredient in an aqueous liquid formulation and the surface-active agent which may also be present in the formulation, mild to severe corrosion of metal surfaces will occur when contacted by the aqueous agricultural compositions.

The term "active agricultural ingredient" as herein employed is inclusive of any ingredient functioning as a plant phytotoxicant or as a plant growth regulant. The particular function of an active ingredient can be that of a herbicide when applied to the plant at moderate to high application rates and, on the other hand, function as a plant growth regulant at low to minute application rates. Such dual function capability is exhibited by some of the aminomethylenephosphonic acids and their agriculturally acceptable salts as described in U.S. Pat. Nos. 3,455,675 and 3,556,762, the former being directed to phytotoxicant use and the latter to plant growth regulation. The herbicidal activity of N-phosphonomethylglycine and its agriculturally acceptable salt and ester derivatives is described in U.S. Pat. Nos. 3,799,758; 3,868,407; 3,971,648 and 3,977,860. Plant growth regulant utility for N-phosphonomethylglycine and its agriculturally acceptable salt and ester derivatives is described in U.S. Pat. Nos. 3,853,530 and 3,988,142.

The aqueous formulations of the aminomethylenephosphonic acids, such as N-phosphonomethylglycine or derivatives thereof, and more particularly those formulations water-diluted to application levels are corrosive to iron, steel or galvanized metal surfaces of containers in which the concentrates or mixtures are stored, and to steel or galvanized surfaces of spraying equipment. Hydrogen evolution is one aspect of the corrosion activity and can cause disruptive pressures in closed containers containing the aqueous agricultural compositions as well as constituting a fire hazard and explosion hazard.

It is known that the application of various organic coatings, such as the phenolics, synthetic rubbers, alkyds, vinyls as well as glass linings to metal surfaces is one practical means for protecting or preventing corrosion of metal surfaces but such coatings increase the cost of containers and other equipment used for application of herbicides or plant growth regulants. Moreover, the integrity of such coatings is subject to accidental or abrasive abuse under agricultural application working conditions whereby the coating is mechanically abraded, scraped or otherwise detached from the metal surface. When this occurs, the exposed metal surface is then readily attacked by the agricultural composition, and such corrosion frequently causes detachment or degradation of the protective coating material adjacent to the exposed metal surface thus accelerating the overall corrosion of the equipment.

Trabanelli et al reported on the performance of various organic sulfur compounds for inhibiting corrosion of iron immersed in sulfuric acid and noted that mercaptans were generally poor inhibitors of iron corrosion and in some instances even functioned as corrosion stimulators (Chemical Abstracts, Volume 72, page 206, 58134z).

It was thus most surprising to discover that thiol compounds, e.g. mercaptans, as well as the ammonium and alkali metal thio salts of inorganic polybasic acids and the thio alkali metal salts are effective inhibitors of metal corrosion for aqueous agricultural compositions containing as an active agricultural ingredient an aminomethylenephosphonic acid, such as N-phosphonomethylglycine or the agriculturally acceptable salt or ester derivatives thereof. Obviously, a satisfactory inhibitor of acidic corrosion as measured by $H_2$ evolution and metal corrosion rate for a herbicidal composition or plant growth regulant composition should not deleteriously modify the agricultural activity of the composition. It was found that both retention of agricultural activity and adequate inhibition of acidic corrosion was obtained by the addition to aqueous formulations of an aminomethylenephosphonic acid or the agriculturally acceptable derivatives of relatively small amounts of certain thio compounds, such as the alkane thiols and dithiols, alkali metal salts of the alkane thiols and dithiols, and the ammonium and alkali metal thio salts of polybasic inorganic acids, i.e., sulfuric acid and phosphoric acid. Adequate inhibition of acidic corrosion as measured by $H_2$ evolution can be obtained with a minimum of about 0.15 percent by weight of the thio compound on the weight of N-phosphonomethylglycine. To insure long term corrosion inhibition, it is preferred to use the thio compound in amounts of 0.3 to 3 percent by weight on the weight of the N-phosphonomethylglycine or aminomethylenephosphonic acid or derivatives thereof although the thio compound can be employed in amounts as high as 20 percent by weight based on the N-phosphonomethylglycine. Not too infrequently, aqueous concentrates of the herbicidal or plant growth regulant compositions may be stored in the vendor's metal containers by the farmer for many months before being used and, hence, it is desirable to minimize corrosion of the container to the maximum extent in order to prevent any possible leakage of the concentrate due to rusting of the container's metal walls. Amounts more than 5 percent by weight of the thio compound can be used if desired but no further commensurate advantage with respect to corrosion is usually realized.

In the agricultural formulations of this invention, one can employ anionic, cationic or non-ionic surface-active agents. The surfactants which are useful in the compositions of this invention include those of the cationic, anionic, and non-ionic variety and also amine oxide, imidazolines, propoxylated ethoxylated ethylenediamine, quaternary ammonium compounds, betaine derivatives as well as amphoteric surfactants. Examples of the amine oxides are lauryldimethylamine oxide, cetyldimethylamine oxide, myristyldimethylamine oxide, bis(2-hydroxyethyl)cocoamine oxide and the like. Examples of quaternary amine surfactants are cocotrimethylammonium chloride, alkylamidoethyl alkyl imidazolium methyl methosulfate. Examples of cationic surfactants are N,N-bis(2-hydroxyethyl)alkylamines where the alkyl groups are $C_{14}-C_{18}$ derived from tallow, N,N-bis($\alpha$-ethyl-omega-hydroxy)-poly(oxyethylene)alkylamines having an average of 3 oxyethylene groups, the alkyl being $C_{14}-C_{18}$ derived from tallow and (3-lauramidopropyl) trimethylammonium methyl sulfate. Some anionic surface-active agents are the sulfated fatty alcohols and the alkylarylsulfonates. Representative of the sulfated fatty alcohols are the sodium or lower alkanol amine salts of the monoesters of sulfuric acid with N-aliphatic alcohols containing from 8 to 18 carbon atoms. The alkylarylsulfonates are inclusive of the products derived from the alkylation of an aromatic hydrocarbon, e.g., benzene, naphthalene, diphenyl, diphenyl methane and phenoxybenzene, sulfonation of the resulting alkylated aromatic hydrocarbon and neutralization of the sulfonation product with NaOH or KOH, or with a primary or secondary amine.

Some non-ionic surface-active agents are the ethoxylated monoamines having the structure

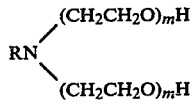

wherein R is alkyl containing from about 8 to 16 carbon atoms and m is an integer from 2 to 25. Preferred anionic surface-active agents are the aliphatic amine salts of monoalkyl ($C_8-C_{16}$) phenoxybenzene disulfonic acids.

All of the alkane thiols and dithiols containing from 2 to 16 carbon atoms in the alkane moiety which have been examined for corrosion inhibition were found effective in substantially eliminating hydrogen evolution under the test conditions herein described. The alkane thiols particularly those containing 8 or less carbon atoms in the alkane moiety have a pronounced disagreeable odor. It is, therefore, preferable to employ alkane thiols having greater than 8 carbon atoms in the alkane moiety. The higher alkane thiols are less odorous and, hence, are preferred in the interests of minimizing worker and user discomfort. The terms "alkane thiol" and "alkane dithiol" are intended to include the normal, secondary and tertiary isomers of these compounds. Representative thiols and dithiols useful in the practice of this invention include 1,2-ethanedithiol, ethanethiol, 1,3-propanedithiol, 1-propanethiol, 2-propanethiol, 2-methyl-2-propanethiol, 1,4-butanedithiol, 1-butanethiol, 3-methyl-1-butanethiol, 1-hexanethiol, 2-hexanethiol, 3-hexanethiol, 1-octanethiol, 2-octanethiol, 1-decanethiol, 1-dodecanethiol and 1-hexadecanethiol. Representative of the alkali metal salts of the alkane thiols and dithiols are the sodium and potassium salts of 1-ethanethiol, 1-butanethiol, 1-hexanethiol and 1-dodecanethiol. Representative of the ammonium and alkali metal thio salts of inorganic polybasic acids are ammonium thiosulfate, ammonium thiophosphate, ammonium thiocarbonate, sodium thiophosphate, potassium thiophosphate, sodium dimethyldithiocarbonate and sodium thiocarbonate, which unlike the alkane thiols do not contain in their structure an—SH group but nevertheless do inhibit hydrogen evolution to a major extent from steel and zinc surfaces. One can also add compounds such as sodium sulfite to the thiosulfate-containing compositions. Although no improvement in the corrosion inhibition is obtained, this prevents dissociation of the ammonium thiosulfate in this composition.

The corrosion inhibited agricultural compositions of this invention, including concentrates requiring dilution with water prior to plant application, contain from 5 to 95 parts by weight of an agriculturally active agent, from about 5 to 95 parts by weight of an adjuvant comprising from 0.25 to 25 parts by weight of a non-ionic or anionic surface-active agent, from 0 to 25 parts by weight of a dispersant and from about 4.5 to about 95 parts by weight of inert liquid extender, e.g., water and from 0.1 to 2 parts by weight of a suitable thio compound. The compositions are prepared by admixing the active ingredient, the thio compound, the surface-active agent and the liquid extender to provide liquid compositions in the form of solutions, suspensions, dispersions or emulsions. These liquid compositions immediately prior to application to plants are diluted with water as required to obtain the desired effects (herbicidal or plant growth regulation).

For determining hydrogen evolution, concentrated liquid formulations were prepared according to the following formula, all parts being by weight:

| | |
|---|---|
| Monoisopropylamine salt of N-phosphonomethylglycine | 41 parts |
| Surfactant | 15 parts |
| Inhibitor | 1 part |
| Water | 43 parts |

The liquid concentrates were then diluted with water to actual spray use concentrations, i.e., 5 parts concentrate to 95 parts water and the diluted formulations were tested for hydrogen evolution and corrosion characteristics. The diluted concentrates are normally more corrosive to metals than the concentrates.

Hydrogen evolution was measured according to the following procedure. A metal coupon (mild steel or zinc) was horizontally supported within the mouth of an inverted plastic funnel, the support being toothpicks fastened to the rim of the funnel. The dimensions of the steel coupon were 3.2 cm×1.4 cm×0.6 cm; the zinc coupons were 3.2 cm×1.4 cm×0.2 cm. The funnel assembly with the supported metal coupon was placed into a 250 ml beaker, and enough dilute liquid agricultural formulation was poured into the beaker to completely submerge the funnel. A 100 ml conical graduated glass centrifuge test tube was filled with the formulation, the end of the tube was then finger sealed, inverted and placed over the neck of the funnel. Hydrgen gas evolving from attack on the metal coupon by the formulation ascends upwardly within the conical section of the funnel, then into the funnel neck and finally into the test tube where it collects and displaces the liquid formulation. The amount of collected gas is read directly off the graduations on the test tube. The beaker and its contents are maintained at room temperature during the 24-hour test period.

The corrosion rate of the coupons was determined by immersing degreased mild steel and zinc coupons in a given formulation at room temperature for 96 hours and then measuring weight loss or gain of the coupon and extrapolating the result to an annual rate of corrosion.

Water-diluted concentrates prepared as described supra and containing the monoisopropylamine salt of N-phosphonomethylglycine as the active agricultural ingredient were modified by the inclusion of various thiol compounds and surfactants as stated in subsequent Table I. Test data reported in Table I was obtained at room temperature.

Table I

| Expt. # | Surfactant* | Weight % Inhibitor in "Concentrate" | Inhibitor | Solution pH | H$_2$ Evolution cc During Initial 24 Hours per sq/ft Metal Surface (929 sq/cm) Steel | Zinc | Corrosion Rate (mm/year) Steel | Zinc |
|---|---|---|---|---|---|---|---|---|
| 1 | A - no inhibitor | | | 4.5 | 15.0 | 2.3 | 0.080 | 0.037 |
| 2 | B - no inhibitor | | | 4.3 | 12.4 | 2.3 | 0.091 | 0.049 |
| 3 | C - no inhibitor | | | 4.3 | 18.0 | 1.4 | 0.218 | 0.068 |
| 4 | A + 1% | | 1-dodecanethiol | 4.5 | 0 | 0 | 0.011 | 0.026 |
| 5 | B + 1% | | 1-dodecanethiol | 4.3 | 0 | 0 | 0.013 | 0.006 |
| 6 | C + 1% | | 1-dodecanethiol | 4.3 | 0 | 0 | 0.017 | 0.008 |
| 7 | C + 1% | | 1-hexadecylthiol | | 0 | 0 | 0.011 | 0.025 |
| 8 | C + 1% | | 1-octanethiol | | 0 | 0 | 0.017 | 0.030 |
| 9 | C + 1% | | 1,12-dodecanedithiol | | 0 | 0 | 0.006 | 0.013 |
| 10 | C + 1% | | sodium salt of dodecanethiol | | 0 | 0 | 0.010 | 0.027 |
| 11 | C + 1% | | dodecanethiol & oxalic acid equal to weight of isopropylamine salt of N-phosphonomethylglycine | | 0 | 0 | 0.020 | 0.045 |
| 12 | C + 1% | | dodecanesulfide | | 0.6 | 0 | 0.035 | 0.040 |
| 13 | C + 1% | | dodecanedisulfide | | 1.9 | 0 | 0.033 | 0.053 |
| 14 | C + 1% | | octanesulfide | | 1.1 | 0 | 0.022 | 0.045 |
| 15 | C + 1% | | octanedisulfide | | 0.1 | 0 | 0.035 | 0.093 |
| 16 | A + 2% | | ammonium thiosulfate | | 0 | 0 | 0.040 | 0.033 |
| 17 | B + 2% | | ammonium thiosulfate | | 0.3 | 0.3 | 0.111 | 0.119 |
| 18 | C + 2% | | ammonium thiosulfate | | 0.3 | 0.3 | 0.155 | 0.058 |
| 19 | C + 1% | | furanomethylthiol | | 0 | 3.6 | 0.058 | 0.10** |
| 20 | C + 1% | | alpha mercaptotoluene | | 0 | 4.1 | 0.043 | 0.075** |
| 21 | C + 1% | | p-thiocresol | | 0 | 0 | 0.033 | 0.048 |
| 22 | C + 1% | | 1-methyl-1-propanethiol | | 0 | 0.6 | 0.040 | 0.033 |
| 23 | C + 1% | | 2-methyl-1-propanethiol | | 0 | 9.8 | 0.038 | 0.040 |
| 24 | A + 1% | | sodium thiophosphate | | 0 | 6.6 | 0.022 | 0.205 |
| 25 | B + 1% | | sodium thiophosphate | | 0.7 | 5.1 | 0.071 | 0.231 |
| 26 | C + 1% | | sodium thiophosphate | | 3.4 | 5.8 | 0.081 | 0.152 |
| 27 | A + 1% | | dimethyldithiocarbamic acid sodium salt | | 0 | 1.8 | 0.020 | 0.099 |
| 28 | B + 1% | | dimethyldithiocarbamic acid sodium salt | | 0 | 5.1 | 0.022 | 0.104 |
| 29 | C + 1% | | dimethyldithiocarbamic acid sodium salt | | 0 | 3.4 | 0.043 | 0.093 |
| 30 | A + 1% | | sodium thiocarbonate | | 0 | 0.5 | 0.022 | 0.086 |
| 31 | B + 1% | | sodium thiocarbonate | | 0.7 | 2.9 | 0.055 | 0.071 |
| 32 | C + 1% | | sodium thiocarbonate | | 0.7 | 1.1 | 0.068 | 0.096 |
| 33 | Distilled water (no | | | | 0.4 | 0.3 | 0.043 | 0.022 |

Table I-continued

| Expt. # | Surf-ac-tant* | Weight % Inhibitor in "Concentrate" | Inhibitor | Solution pH | H₂ Evolution cc During Initial 24 Hours per sq/ft Metal Surface (929 sq/cm) | | Corrosion Rate (mm/year) | |
|---|---|---|---|---|---|---|---|---|
| | | | | | Steel | Zinc | Steel | Zinc |
| | | inhibitor) | | | | | | |

*Surfactant "A" is a non-ionic type surfactant comprising an ethoxylated tallow amine having the structure

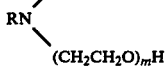

wherein m has an average value of between 15 and 20 and R is alkyl having an average number of carbon atoms of about 17-18.
Surfactant "B" is an anionic type surfactant comprising a mixture which averages about 80 percent or more by weight of a monoisopropylamine salt of $C_{10}$ alkyl phenoxybenzene disulfonic acid and up to about 20 percent by weight of dialkylated products of phenoxybenzene disulfonic acid.
Surfactant "C" is also an anionic surfactant and is the triethanolamine salt of a ($C_{8-10}$) alcohol sulfate; ($C_{8-10}$) $OSO_2ON(CH_2CH_2OH)_3$.
                                                                                                                     H

**Weight gain.

Inspection of the data presented in Table I shows that all the tested alkane thiols and dithiols (Experiments 4–9) and the alkali metal salt of an alkane thiol (Experiment 10) were 100 percent effective in preventing evolution of hydrogen on test coupons of steel and zinc. Additionally, they exhibited the lowest corrosion rates of steel and zinc of all the tested inhibitors being less corrosive than even distilled water per se (Experiment 33).

Almost as effective as the thiol and dithiols and alkali metal salts of the thiols in reducing H₂ evolution was ammonium thiosulfate (Experiments 16, 17 and 18), sodium thiophosphate (Experiments 24, 25 and 26), sodium thiocarbonate (Experiments 30, 31 and 32) and sodium dimethyldithiocarbamate (Experiments 27, 28 and 29). Inhibition of corrosion, however, was only fair. The inhibition of H₂ evolution is adequate for safe storage of the ammonium thiosulfate, the sodium thiophosphate and the sodium thiocarbonate inhibited formulations in metal cans, tanks and other metal equipment.

Experiment 11 involved a herbicidal formulation containing in addition to the dodecanethiol inhibitor, the copresence of oxalic acid in an amount equal to the weight of the isopropylamine salt of N-phosphonomethylglycine. The use of oxalic acid in herbicidal formulations containing N-phosphonomethylglycine or its derivatives is disclosed in "Research Disclosure" publication number RD15334, published January, 1977 by Industrial Opportunites Ltd., Homewell-Havant-Hampshire P09 1EF, United Kingdom. According to said publication, when herbicidal formulations containing N-phosphonomethylglycine or its derivatives are diluted for application purposes with hard water, i.e. water containing calcium or magnesium ions in the range of from 100 to 2000 or more parts by weight per million parts by weight of water, the diluted formulations have diminished herbicidal activity as compared to the same formulations diluted with deionized water. The publication teaches the use of oxalic acid in hard water diluted herbicidal formulations to restore the herbicidal activity and recommends the amount of oxalic acid be at least equivalent to 50 percent of the calcium or magnesium ion to as much as 200 percent or more of such ions present in the diluting hard water. The weight ratio of the N-phosphonomethylglycine compound to oxalic acid ranges from 1 to 10 parts by weight of the glycine compound per 1 to 10 parts by weight of oxalic acid. Oxalic acid is known to be corrosive of iron surfaces. As demonstrated by the data in Table I for Experiment 11, the normal corrosive action of oxalic acid on iron surfaces is satisfactorily inhibited when a thiol compound is present in the herbicidal formulation.

That the use of thio compounds as inhibitors of metal corrosion in herbicidal compositions containing an amine salt of N-phosphonomethylglycine does not significantly diminish post-emergent herbicidal activity of the composition is quite evident from the data presented in Table II on the post-emergence killing of quackgrass using formulations described in Table I, being Experiments 1 to 6 and 16 to 18. The experimental formulations were suitably diluted with water and applied to quackgrass plants established from vegetative propagules at a rate of 187 liters per hectare. Plants treated with the experimental formulations were placed in a greenhouse as observed and recorded 12 days after treatment with the herbicidal formulation.

Table II

| Experiment Number | Surfactant | Inhibitor | Rate (kg/h)* | % Inhibition Plant Response (% Quackgrass 12 Days After Treatment) |
|---|---|---|---|---|
| 1 | A | None | 1.12 | 95 |
| | | | 0.56 | 95 |
| | | | 0.28 | 40 |
| 2 | B | None | 1.12 | 99 |
| | | | 0.56 | 99 |
| | | | 0.28 | 50 |
| 3 | C | None | 1.12 | 99 |
| | | | 0.56 | 99 |
| | | | 0.28 | 60 |
| 4 | A | Dodecane-thiol | 1.12 | 98 |
| | | | 0.56 | 98 |
| | | | 0.28 | 45 |
| 5 | B | Dodecane-thiol | 1.12 | 99 |
| | | | 0.56 | 98 |
| | | | 0.28 | 70 |
| 6 | C | Dodecane-thiol | 1.12 | 99 |
| | | | 0.56 | 99 |
| | | | 0.28 | 55 |
| 16 | A | Ammonium thiosulfate | 1.12 | 99 |
| | | | 0.56 | 98 |
| | | | 0.28 | 60 |
| 17 | B | Ammonium thiosulfate | 1.12 | 99 |
| | | | 0.56 | 90 |
| | | | 0.28 | 60 |
| 18 | C | Ammonium thiosulfate | 1.12 | 99 |
| | | | 0.56 | 99 |
| | | | 0.28 | 40 |

*Amount of monoisopropylamine salt of N-phosphonomethylglycine applied per hectare.

In order to determine that effect on post-emergence herbicidal activity would result when the quantity of thiol inhibitor in a herbicidal formulation containing the monoisopropylamine salt of N-phosphonomethylglycine as the active ingredient was increased many fold beyond that required for adequate inhibition of hydrogen evolution and metal corrosion, two control formulations were prepared, one containing previously described surfactant "A" and the other surfactant "C" according to the following formula, all parts being by weight:

| | |
|---|---|
| Monoisopropylamine salt of N-phosphonomethylglycine | 41 parts |
| Surfactant | 15 parts |
| Water | 44 parts |

The formulations were then diluted with water and sufficient additional surfactant added to the diluted formulations for the surfactant to constitute in each instance 1 percent by weight of the diluted formulation. The amount of water used to prepare the diluted formulations was so adjusted that each diluted formulation could be spray applied to the plants at a common rate of 187 liters per hectare, even though the amount of active ingredient in each diluted formulation was maintained at different levels. The amount of thiol inhibitor in each diluted formulation was also adjusted to maintain a constant application of 4.48 kilograms per hectare when the diluted formulation was spray applied at 187 liters per hectare. The diluted formulations (with and without inhibitor) were sprayed of 3 week old greenhouse grown Johnson grass and quackgrass and the observations as to herbicidal effectiveness reported in Table III were made 28 days later.

Table III

| Formulation | | Rate | % Inhibition | |
|---|---|---|---|---|
| Surfactant | Inhibitor | (kg/h)* | Johnson Grass | Quackgrass |
| A | None | 0.28 | 100 | 100 |
| A | None | 0.14 | 65 | 98 |
| A | None | 0.07 | 35 | 25 |
| A | None | 0.035 | 0 | 20 |
| C | None | 0.28 | 95 | 100 |
| C | None | 0.14 | 60 | 95 |
| C | None | 0.07 | 30 | 35 |
| C | None | 0.035 | 0 | 20 |
| A | Octanethiol | 0.28 | 85 | 100 |
| A | Octanethiol | 0.14 | 55 | 65 |
| A | Octanethiol | 0.07 | 30 | 15 |
| A | Octanethiol | 0.035 | 0 | 0 |
| C | Octanethiol | 0.28 | 85 | 75 |
| C | Octanethiol | 0.14 | 35 | 45 |
| C | Octanethiol | 0.07 | 20 | 30 |
| C | Octanethiol | 0.035 | 0 | 0 |
| A | 1,12-Dodecanedithiol | 0.28 | 90 | 100 |
| A | 1,12-dodecanedithiol | 0.14 | 60 | 90 |
| A | 1,12-dodecanedithiol | 0.07 | 15 | 25 |
| A | 1,12-dodecanedithiol | 0.035 | 0 | 15 |
| C | 1,12-dodecanedithiol | 0.28 | 85 | 100 |
| C | 1,12-dodecanedithiol | 0.14 | 35 | 70 |
| C | 1,12-dodecanedithiol | 0.07 | 20 | 40 |
| C | 1,12-dodecanedithiol | 0.035 | 0 | 20 |

*Amount of monoisopropylamine salt of N-phosphonomethylglycine applied her hectare.

Although the amount of thiol inhibitor to active ingredient of the formulations described in Table III ranged from 164:1 at the 0.28 kg/h rate to a high of 1312:1 at the 0.035 kg/h rate of active ingredient, only a slight diminution of herbicidal effectiveness was observed and this occurred principally at ratios of thiol inhibitor to active ingredient of more than 164:1.

Although the inhibitor efficacy of various thio compounds was exemplified with the monoisopropylamine salt of N-phosphonomethylglycine in Table I, substantially similar corrosion inhibition can be expected when a thio compound as herein disclosed is admixed with other salts and esters of N-phosphonomethylglycine such as the alkali metal salts as are disclosed in U.S. Pat. No. 3,977,860. Such salts and esters include but are not limited to the following: monocyclohexylamine salt of N-phosphonomethylglycine di(methylamine) salt of N-phosphonomethylglycine di(dimethylamine) salt of N-phosphonomethylglycine di(ethylamine) salt of N-phosphonomethylglycine di(n-propylamine) salt of N-phosphonomethylglycine di(morpholine) salt of N-phosphonomethylglycine mono(stearlyamine) salt of N-phosphonomethylglycine mono(tallowamine) salt of N-phosphonomethylglycine mono(methylbutyl) salt of N-phosphonomethylglycine mono(butylamine) salt of N-phosphonomethylglycine n-dibutylamine salt of N-phosphonmethylglycine n-octadecylamine salt of N-phosphonomethylglycine methoxyethylamine salt of N-phosphonomethylglycine ethylenediamine salt of N-phosphonomethylglycine dipropanolamine salt of N-phosphonomethylglycine chloroethylamine salt of N-phosphonomethylglycine phenoxyethylamine salt of N-phosphonomethylglycine mono(triethylamine) salt of N-phosphonomethylglycine mono(diethylenetriamine) salt of N-phosphonomethylglycine monoisopropylamine salt of N-phosphonomethylglycine monomorpholine salt of N-phosphonomethylglycine monoaniline salt of N-phosphonomethylglycine monoethanolamine salt of N-phosphonomethylglycine monodiethanolamine salt of N-phosphonomethylglycine monoammonium salt of N-phosphonomethylglycine monosodium salt of N-phosphonomethylglycine disodium salt of N-phosphonomethylglycine trisodium salt of N-phosphonomethylglycine monopotassium salt of N-phosphonomethylglycine dipotassium salt of N-phosphonomethylglycine tripotassium salt of N-phosphonomethylglycine dilithium salt of N-phosphonomethylglycine monosidodium salt of ethyl N-phosphonomethylglycinate monosidium salt of chloroethyl N-phosphonomethylglycinate methyl N-phosphonomethylglycinate dimethyl N-phosphonomethylglycinate ethyl N-ohosphonomethylglycinate 2-chloroethyl N-phosphonomethylglycinate n-propul N-phosphonomethylglycinate n-butyl N-phosphonomethylglycinate
n-hexyl N-phosphonomethylglycinate
cyclohexyl N-phosphonomethylglycinate
n-octyl N-phosphonomethylglycinate
n-decyl N-phosphonomethylglycinate
b-dodecyl N-phosphonomethylglycinate Representative but not inclusive of the aminophosphonates described in U.S. Pat. No. 3,556,762 and which in aqueous formulations caise corrosion of metal surfaces are the following compounds:
nitrilodi(acetic acid) methylphosphonic acid)
tris(dimethylammonium)iminoacetate N-methylphosphonate
trisodium iminodiacetate N-methylphosphonate tetra(dimethylammonium)aminoacetate N,N-bis-methylphosphonate
2,2'-bisphosphonomethyliminoacetic acid
dipotassium iminidiacetate N-methyl-O-potassium-O-ethyl-phosphonate Data on hydrogen evolution and corrosion inhibition by dodecanethiol for several agricultural formulations containing as an active ingredient N-phosphonomethylglycine or salt or ester derivature thereof or an aminophosphonate compound are tabulated in Table IV. The formulations used in Table IV were of two types, liquid and dry powder. Experiments 34 and 35 were conducted on liquid formulations of the following compositions, all parts being by weight:

| Experiment 34 | |
|---|---|
| Di-(monoisopropylamine) salt of N-phosphonomethylglycine | 41 |
| Surfactant "C" | 15 |
| Water | 44 |

| Experiment 35 | |
|---|---|
| Di-(monoisopropylamine salt of N-phosphonomethylglycine | 41 |
| Surfactant "C" | 15 |
| Dodecanethiol | 1 |
| Water | 43 |

The dry powder formulations, Experiments 36 to 47 had the following compositions, all parts being by weight:

| Experiment 36 | |
|---|---|
| Disodium salt of N-phosphonomethylglycine | 78 |
| Surfactant "D" | 2 |
| Urea | 20 |

| Experiment 37 | |
|---|---|
| Disodium salt of N-phosphonomethylglycine | 78 |
| Surfactant "D" | 2 |
| Dodecanethiol - Urea Complex (2.1 parts thiol) (7.1 parts urea) | 9.2 |
| Urea | 10.9 |

| Experiment 38 | |
|---|---|
| Diammonium salt of N-phosphonomethylglycine | 74.6 |
| Surfactant "D" | 2 |
| Urea | 23.4 |

| Experiment 39 | |
|---|---|
| Diammonium salt of N-phosphonomethylglycine | 74.6 |
| Surfactant "D" | 2 |
| Dodecanethiol Urea Complex (2.1 parts thiol) (7.1 parts urea) | 9.2 |
| Urea | 14.3 |

| Experiment 40 | |
|---|---|
| Dipotassium salt of N-phosphonomethylglycine | 89.7 |
| Surfactant "D" | 2 |
| Urea | 8.3 |

| Experiment 41 | |
|---|---|
| Dipotassium salt of N-phosphonomethylglycine | 87.7 |
| Surfactant "D" | 2 |
| Dodecanethiol - Urea Complex (2.1 parts thiol) (7.1 parts urea) | 9.2 |
| Urea | 1.2 |

| Experiment 42 | |
|---|---|
| N-phosphonomethylglycine | 64.4 |
| Surfactant "D" | 2 |
| Urea | 33.6 |

| Experiment 43 | |
|---|---|
| N-phosphonomethylglycine | 64.4 |
| Surfactant "D" | 2 |
| Dodecanethiol - Urea Complex (2.1 parts thiol) (7.1 parts urea) | 9.2 |
| Urea | 22.4 |

| Experiment 44 | |
|---|---|
| 2,2'-bisphosphonomethyliminoacetic acid | 51 |
| Surfactant "D" | 2 |
| Urea | 47 |

| Experiment 45 | |
|---|---|
| 2,2'-bisphosphonomethyliminoacetic acid | 51 |
| Surfactant "D" | 2 |
| Dodecanethiol - Urea Complex (2.1 parts thiol) (7.1 parts urea) | 9.2 |

-continued

Experiment 45

| | |
|---|---|
| Urea | 37.9 |

Experiment 46

| | |
|---|---|
| Monoethyl ester of N-phosphonomethylglycine | 86.3 |
| Surfactant "D" | 2 |
| Urea | 11.7 |

Experiment 47

| | |
|---|---|
| Monoethyl ester of N-phosphonomethylglycine | 86.3 |
| Dodecanethiol - Urea Complex (2.1 parts thiol) (7.1 parts urea) | 9.2 |
| Urea | 2.5 |

Surfactant "C" is as previously described.
Surfactant "D", an anionic surfactant, is a complex of sodium dioctyl-sulfosuccinate.

Experiments 34, 36, 38, 40, 42 and 44 were control experiments containing no inhibitor. Experiments 37, 39, 41, 43 and 45 were dry solid formulations containing a complex of urea and dodecanethiol. Alkane thiols such as dodecanethiol are substantially water insoluble and although a surfactant is an aid in effecting dispersion of the thiol in an aqueous formulation, it has been found that a solid complex of urea and a straight chain alkane thiol when mixed with a dry mixture of the active ingredient and surfactant enhances dispersibility of the thiol in aqueous agricultural formulations and minimizes separation of the thiol component. The complex dissolves readily in water to reform the urea and the thiol with the thiol being finely dispersed and remaining in suspension. The urea-thiol complex is prepared by dissolving the alkane thiol in a solvent such as isoctane and mixing the solution at room temperature with sufficient urea prewetted with methanol until the urea increases in volume; the reaction is slightly exothermic. The molar ratio of urea to alkane thiol used to form the complex is proportional to the thiol's chain length being at least 6:1 for alkane thiols containing 6 carbon atoms, 10:1 moles for dodecanethiol and about 16:1 for thiols of 16 carbon atoms. The solvents used in the reaction are removed by washing and drying. The corrosion experiments reported in Table IV were all conducted with the liquid as well as the solid type formulations having been diluted with water in amount corresponding to normal application dilutions, namely a dilution that would apply per hectare 2.24 kilograms of active ingredient (calculated as N-phosphonomethylglycine or 2,2'-bisphosphonomethyliminoacetic acid) at a spraying rate of 187 liters per hectare.

Table IV

| Ex. No. | Surfactant | Active Ingredient | Inhibitor | pH | $H_2$ Evolution cc/sq.ft. from Steel 0–24 Hours | $H_2$ Evolution cc/sq.ft. from Zinc 0–24 Hours | Corrosion Rate (mm/hr) Steel | Corrosion Rate (mm/hr) Zinc |
|---|---|---|---|---|---|---|---|---|
| 34 | C | Diisopropylamine salt of N-phosphonomethylglycine | None | 7.17 | 5.3 | 1.8 | 0.266 | 0.320 |
| 35 | C | " | Dodecanethiol | 7.10 | 0 | 0 | 0.012 | 0.005 |
| 36 | D | Disodium salt of N-phosphonomethylglycine | None | 6.54 | 4.99 | 0 | 0.172 | 0.055 |
| 37 | D | " | Dodecanethiol | 6.79 | 0 | 0 | 0.017 | 0.017 |
| 38 | D | Diammonium salt of N-phosphonomethylglycine | None | 6.56 | 5.20 | 0.60 | 0.132 | 0.045 |
| 39 | D | " | Dodecanethiol | 6.60 | 0 | 0 | 0.010 | 0.010 |
| 40 | D | Dipotassium salt of N-phosphonomethylglycine | None | 6.70 | 6.19 | 0.8 | 0.0812 | 0.035 |
| 41 | D | Dipotassium salt of N-phosphonomethylglycine | Dodecanethiol | 6.79 | 0 | 0 | 0.007 | 0.002 |
| 42 | D | N-phosphonomethylglycine | None | 2.17 | 4.3 | 89.9 | 0.010 | 2.029 |
| 43 | D | " | Dodecanethiol | 2.14 | 0 | 0.8 | 0.003 | 0.187 |
| 44 | D | 2,2'-bisphosphonomethyliminoacetic acid | None | — | 233 | 720 | 6.45 | 23.3 |
| 45 | D | " | Dodecanethiol | — | 0 | 2.9 | 0.030 | 0.038 |

Table IV-continued

| Ex. No. | Surfactant | Active Ingredient | Inhibitor | pH | H₂ Evolution cc/sq.ft. from Steel 0-24 Hours | H₂ Evolution cc/sq.ft. from Zinc 0-24 Hours | Corrosion Rate (mm/hr) Steel | Corrosion Rate (mm/hr) Zinc |
|---|---|---|---|---|---|---|---|---|
| 46 | D | Monoethyl ester of N-phosphonomethylglycine | None | — | 0.6 | 0.5 | 0.040 | 0.063 |
| 47 | D | " | Dodecanethiol | — | 0 | 0 | 0.020 | 0.030 |

Thiols other than the alkane thiols have also been found effective in inhibiting corrosion by aqueous agricultural compositions as herein contemplated. Such thiols include the aromatic and cycloaliphatic thiols. For example, 2% inhibiting amounts of p-chlorothiophenol, 2-aminothiophenol, 2-furanomethanethiol, toluenethiol, 2-benzoxazolthiol and mercaptobenzothiazole enable a dry disodium salt of N-phosphonomethylglycine formulation corresponding to Experiment 36 when diluted with water reduces the hydrogen evolution and the metal corrosion rate. Similar corrosion inhibition was obtained when fertilizer diluent ingredients other than urea were included in the agricultural formulations, as, for example, monoammonium phosphate and disodium phosphate.

Although the invention is described with respect to specific modifications, the details thereof are not to be construed as limitations except to the extent indicated in the following claims.

What is claimed is:

1. A herbicidal or plant growth regulant composition comprising an active ingredient selected from the aminomethylenephosphonic acids of the formula

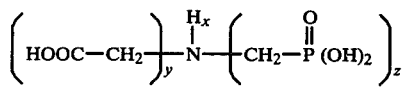

wherein y and z are each individually 1 or 2, and x is 0 or 1, the sum of x, y and z being 3, and the agriculturally acceptable salts and esters thereof, at least one of water or a surfactant, and a metal corrosion inhibiting amount of a thio compound selected from alkane thiols having from 2 to 16 carbon atoms in the alkane moiety, aromatic thiols, the alkali metal salts of said thiols and the ammonium and alkali metal thio salts of polybasic inorganic acids.

2. An composition according to claim 1 wherein the alkane thiol is 1-dodecanethiol.

3. An composition according to claim 1 wherein the alkane thiol is 1-octanethiol.

4. An composition according to claim 1 wherein the alkane thiol is 1-hexadecylthiol.

5. An composition according to claim 1 wherein the ammonium thio salt is ammonium thiosulfate.

6. An composition according to claim 1 wherein the ammonium thio salt is ammonium thiophosphate.

7. An composition according to claim 1 wherein the amount of the thio compound is between 0.15 and 3 percent by weight of the active ingredient.

8. A composition according to claim 1 containing, in addition, between 1 and 10 parts by weight of oxalic acid per 1 to 10 parts by weight of an amine salt of N-phosphonomethylglycine.

9. A dry composition according to claim 1 wherein the thiol is a straight chain alkane thiol and complexed with urea.

10. An composition according to claim 1 wherein the active ingredient is N-phosphonomethylglycine.

11. An composition according to claim 1 wherein the active ingredient is 2,2'-bisphosphonomethyliminoacetic acid.

12. An composition according to claim 1 wherein the active ingredient is a salt of N-phosphonomethylglycine.

13. An composition according to claim 12 wherein the salt is the monoisopropylamine salt of N-phosphonomethylglycine.

14. A method for inhibiting corrosion of iron and zinc metal surfaces in contact with an aqueous herbicidal and plant growth regulant composition comprising water, a surfactant and an active ingredient selected from the aminomethylenephosphonic acids of the formula

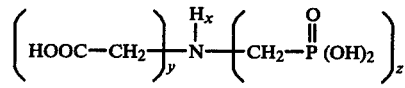

wherein y and z are each individually 1 or 2, and x is 0 or 1, the sum of x, y and z being 3, and the agriculturally acceptable salts and esters thereof which comprises adding to the composition an inhibiting amount of a thio compound selected from alkane thiols having from 2 to 16 carbon atoms in the alkane moiety, aromatic thiols, the alkali metal salts of said thiols and the ammonium and alkali metal thio salts of polybasic inorganic acids.

15. A method in accordance with claim 14 wherein the alkane thiol is 1-dodecanethiol.

16. A method in accordance with claim 14 wherein the alkane thiol is 1-octanethiol.

17. A method in accordance with claim 14 wherein the alkane thiol is 1-hexadecylthiol.

18. A method in accordance with claim 14 wherein the thio compound is ammonium thiosulfate.

19. A method in accordance with claim 14 wherein the thio compound constitutes between 0.15 and 3 percent by weight of the aminomethylenephosphonic acid, or the salts or esters thereof.

20. A method in accordance with claim 14 wherein the thiol is an alkane thiol complexed with urea and the urea-thiol complex is admixed with a dry mixture of the active ingredient and the surfactant before dispersing in water.

21. A method which comprises contacting a plant with a phytotoxic amount of an agueous herbicidal composition comprising an amine salt of N-phosphonomethylglycine, a surfactant and a metal corrosion inhibiting amount of a thio compound selected from alkane thiols having from 2 to 16 carbon atoms in the alkane moiety, aromatic thiols, the alkali metal salts of said thiols and the ammonium and alkali metal thio salts of polybasic inorganic acids.

22. A method according to claim 21 wherein the thio compound constitutes between 0.15 and 3 percent by weight of the amine salt of N-phosphonomethylglycine.

23. A method according to claim 21 wherein the amine salt is the monoisopropylamine salt of N-phosphonomethylglycine.

24. A method which comprises contacting a plant with a plant growth regulating amount of an aqueous plant growth regulating composition comprising a compound selected from the aminomethylenephosphonic acids having the formula

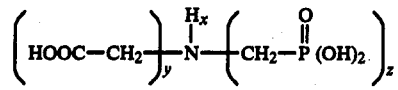

wherein y and z are each individually 1 or 2, and x is 0 or 1, the sum of x, y and z being 3, and the agriculturally acceptable salts and esters thereof, a surfactant, and metal corrosion inhibiting amount of a thio compound selected from alkane thiols having from 2 to 16 carbon atoms in the alkane moiety, aromatic thiols, the alkali metal salts of said thiols and the ammonium and alkali metal thio salts of polybasic inorganic acids.

* * * * *